United States Patent [19]
Lew et al.

[11] Patent Number: 5,607,684
[45] Date of Patent: Mar. 4, 1997

[54] MANUFACTURE OF BAIT WITH HOT MELT BINDER

[75] Inventors: Chel W. Lew, San Antonio, Tex.; Kelly S. Johns, Hahira, Ga.

[73] Assignee: Micro Flo Company, Mulberry, Fla.

[21] Appl. No.: 468,237

[22] Filed: Jun. 5, 1995

Related U.S. Application Data

[63] Continuation-in-part of Ser. No. 784,506, Oct. 31, 1991, Pat. No. 5,484,587, Ser. No. 189,355, Jan. 31, 1994, Pat. No. 5,571,522, and Ser. No. 194,358, Feb. 8, 1994.

[51] Int. Cl.$^6$ ..................................................... A01N 25/00
[52] U.S. Cl. ..................... 424/405; 424/410; 424/419; 424/84
[58] Field of Search .................................. 424/405, 410, 424/419, 84

[56] References Cited

U.S. PATENT DOCUMENTS

| | | |
|---|---|---|
| 2,687,365 | 8/1954 | Link . |
| 2,770,067 | 11/1956 | Lindblom . |
| 3,252,785 | 5/1966 | Hoblit . |
| 3,272,696 | 9/1966 | O'Connell . |
| 3,272,698 | 9/1966 | Lemin et al. . |
| 3,496,272 | 8/1970 | Kruger . |
| 4,049,460 | 9/1977 | Broadbent . |
| 4,237,113 | 12/1980 | Cardarelli ............................ 424/419 |
| 4,238,484 | 12/1980 | Stein et al. . |
| 4,320,130 | 3/1982 | Balsley et al. . |
| 4,440,746 | 4/1984 | Maglio . |
| 4,514,960 | 5/1985 | Sears ........................................ 424/84 |
| 4,615,883 | 10/1986 | Nelsen et al. . |
| 4,764,372 | 8/1988 | Herrnstadt et al. . |
| 4,815,923 | 3/1989 | Lush . |
| 4,834,977 | 5/1989 | Kohama et al. . |
| 4,985,413 | 1/1991 | Kohama et al. . |
| 4,992,275 | 2/1991 | Lush . |
| 5,120,540 | 6/1992 | Doane et al. . |
| 5,244,669 | 9/1991 | Satoh et al. . |
| 5,290,556 | 3/1994 | McKibben et al. ..................... 424/410 |

FOREIGN PATENT DOCUMENTS

| | | |
|---|---|---|
| 1195922 | 10/1985 | Canada . |
| 0228228 | 8/1987 | European Pat. Off. . |
| 56-15204 | 7/1979 | Japan . |
| 59-67209 | 8/1982 | Japan . |
| 85/04074 | 9/1985 | WIPO . |

OTHER PUBLICATIONS

Corn Insects Project, "Limited Field Trials of Semiochemical-based Bait for Control of Adult Northern and Western Corn Rootworms", presentation to NCR–46 Corn Rootworm Technical Committee, Indianapolis, Indiana, Jan. 16–17, 1990.
Corn Insects Projects, "Effects of Particle Size, Distribution nad Attractant Content on Efficacy of Semiochemical–based Baits In Walk–in Field Cages", presentation to NCR–46 Corn Rootworm Technical Committee, Grand Rapids, Michigan, Jan. 16–17, 1990.
Corn Insects Project, "Field Cage and Laboratory Evaluation of Semiochemical–based Baits", presentation to NCR–46 Corn Rootworm Technical Committee, Minneapolis, Minnesota, Jan. 24–25, 1989.
Weissling et al., "Summary of 1988 Experiments with Starch Encapsulated Semiochemicals and Insecticides", Report to the NCR–46 Corn Rootworm Technical Committee, Minneapolis, Minnesota, Jan. 24–25, 1989.
Aguinagalde et al., "Chemosystematic Survey of Cultivated Cucurbita Species" Journal of Horticultural Science, 65(6):6498–955 (1990).
Alves et al., "After–Ripening Effect on Seed Germination and Viability of Curcurbita foetidissima Seed", reprinted from Turrialba, vol. 22, No. 2, pp. 207–209 (Apr.–Jun. 1972).
Anderson et al., "Identification To A Volatile Attractant For Diabrotica and Acalymma SPP From Blossoms of Cucurbita maxima Duchesne", Journal of Chemical Ecology, vol. 12, No. 3, pp. 687–699 (1986).
Anderson et al., "Factors Influencing Distribution of Diabrotica SPP In Blossoms of Cultivated Cucubita SPP", Journal of Chemical Ecology, vol. 1e, No. 4, pp. 681–699 (1987).
Arisawa et al., "Plant Anticancer Agents XXX: Cucurbitacins from Ipomopsis aggregata Polemoniaceae)", Journal of Pharmaceutical Sciences, vol. 73, No. 3, pp. 411–413 (Mar. 1984).
Arthur, "New Approach To Rootworm Control: Manipulating Adult Populations may One Day Greatly Enhance Corn Rootworm Control", Farm Chemicals (Jul. 1989).
Ba–Amer et al., "Fruit and Seed Development in Cucubita foetidissima" Econ. Botany, vol. 22, pp. 297–299 (1968).
Berry, et al., "Buffalo Group Research Status and Potential for Commercialization as a Cucurbitacin Source", University of Arizona (Apr. 1985).
Berry et al., "Buffalo Gourd Roots: Chemical Composition and Seasonal Changes in Starch Content", J. Agric. Food Chem, vol. 26, No. 2, pp. 354–356 (1978).

*Primary Examiner*—Mark D. Sweet
*Attorney, Agent, or Firm*—Banner & Witcoff, Ltd.

[57] ABSTRACT

Baits useful in the control of insect populations are made by a process that includes the steps of: (a) forming droplets of a homogeneous, substantially water-free mixture comprising: (i) 0.01–99 wt % of a feeding stimulant in the form of a finely divided particulate or liquid; (ii) 0.01–99 wt % of an insecticide; and (iii) a molten, polymeric binder composition that is solid at 25° C. and exhibits a melting point within the range from about 35° C. to about 65° C.; and (b) making particulate baits from the droplets by cooling the droplets to a temperature below the melting point of the mixture. The absence of added water permits the use of active insecticidal ingredients that are generally temperature sensitive to the drying temperatures needed for commercial spray drying operations as well as those sensitive to the presence of water during extended storage and transport periods. The use of the present water-free process avoids hydrolysis of the active insecticide during those periods.

18 Claims, No Drawings

OTHER PUBLICATIONS

Berry et al., "Cucurbit Root Starches: Isolation and Some Properties of Starches from *Cucurbita foetidissima* HKB and *Cucurbita digitata* Gray," J. Agric. Food Chem., vol. 23, No. 4, pp. 825–826 (1975).

Brusko, "He Tells EPA What To Do: Better systems, fewer products are the key to safer, more profitable farming, this farmer says", The New Farm Magazine, pp. 11–16 (Nov/Dec 1989).

Castle et al., "Field and Laboratory Transmission of Watermelon Mosaic Virus 2 and Zucchini Yellow Mosaic Virus by Various Aphid Species", The American Phytopathological Society, vol. 82, No. 2, pp. 235–240 (1992).

Daghir et al., "Buffalo Gourd (*Cucurbita foetidissima*) Meal: Nutritive Value and Detoxification", Nutrition Reports International, vol. 21, No. 6, pp. 836–847 (Jun. 1980).

David et al., "Letters to the Editor: Bitter Principles of Cucurbitaceae", Abstracts, pp. 295–297 (1955).

Deheer et al., "Affinity of Spotted Cucumber Beetle (Coleoptera: Chrysomelidae) Larvae to Cuburitacins", Entomological Society of America, pp. 1173–1175 (1991).

Delouche et al., "The Tetrazolium Test For Seed Viability", Mississippi Agricultural Experiment Station Technical Bulletin, pp. 1–63 (1962).

Dreher et al., "Nutritional Evaluation of Buffalo Gourd Root Starch", Nutrition Reports International, vol. 23, No. 1, pp. 1–9 (Jan. 1981).

Dreher et al., "Buffalo Gourd Root Starch: Part I. Properties and Structure", Starch/Starke 35, Nr. 3, pp. 76–81 (1983).

Dreher et al., "Buffalo Gourd Root Starch: Part II. Rheologic Behavior, Freeze–Thaw Stability and Suitability for Use in Food Products", Starch/Starke 35, Nr. 5, pp. 157–162 (1983).

Dunkle et al., "Starch–Encapsulated *Bacillus thuringiensis*: A Potential New Method for Increasing Environmental Stability of Entomopathogens", Environ. Entom., vol. 17, No. 1, 120–126 (1988).

East et al., "Evaluation of screening methods and search for resistance in muskmelon *Cucumis melo* L., to the two–spotted spider mite, *Tetranychus urticae* Koch", Crop Protection, vol. 11, pp. 39–44 (Feb. 1992).

Enslin, "Bitter Principles of the Cucurbitaceae I.—Observations on the Chemistry of Cucurbitacin A", J. Sci. Food Agric. 5, pp. 410–416 (Sep. 1954).

Ferguson et al., "A Report of Cucurbitacin Poisonings in Humans", CGC 6:73–74 (1983).

Ferguson et al., "Cucurbitacins Plant–Derived Defense Compounds for Diabroticites (Coleopter: Chrysomelidae)", Journal of Chemical Ecology, vol. II, No. 3, pp. 311–319 (1985).

Ferguson et al., "Disposition and Fate of Cucurbitacin B in Five Species of Diabroticites", Journal of Chemical Ecology, vol. II, No. 9, pp. 1307–1321 (1985).

Gitter et al., "Studies on The Antitumor Effect of Cucurbitacins", Cancer Research, vol. 21, pp. 516–521 (May 1961).

Guha et al., "The Cucurbitacin–A Review", The Plant Biochemical Journal 2(1):12–28 (1975).

Harrington, "Effect of Fruit Maturity and Harvesting Methods on Germination of Muskmelon Seed", American Society for Horticultural Science, vol. 73, pp. 422–430 (Oct. 1958).

Hawthorne, "Effects of Cultural Practices on the Incidence of Storage Roots in Cucurbita SPP.", New Zealand Journal of Crop and Horticultural Science, vol. 17:49–54 (1989).

Hest, "Rootworms May Die for Love Potion No. 9", The Farmer, 103(13):27 (Aug. 1987).

Holmes, "Germination of Seeds Removed from Mature and Immature Butternut Squashes After Seven Months of Storage", The American Society for Horticultural Science, vol. 62, pp. 232–236 (1953).

Howe et al., "Western Corn Rootworm Adult and Spotted Cucumber Beetle Associations with Cucurbita and Cucurbitacins", Environmental Entomology, vol. 5, No. 6, pp. 1043–1048 (Dec. 1976).

Hummel et al., "Secondary Plant Factors of Cucurbita Species suppress Sex Attraction in the Beetle Diabrotica Under Cimpunctata Howardi", Proc. 5th Int. Symp. Insect–Plant Relationships, Washington, pp. 163–167 (1982).

Hutta et al., "The Determination of Bitter Principles in Zucchinis", J. Sci. Food Agric. vol. 36, pp. 1107–1112 (1985).

Hylands et al., "Cucurbitacin S. A New Cucurbitacin From Bryonia Dioica", Phytochemistry, vol. 15, pp. 559–560, (1976).

Hylands et al., "$3\alpha$–Hydroxy–Multiflora–7, 9(11)–Dien–$29\alpha$–OIC Acid, A New Triterpene from Bryonia Dioica", Phytochemistry, vol. 18, pp. 1843–1845 (1979).

Hylands et al., "Bryocoumaric Acid, a New Triterpene from Bryonia dioica", reprinted from Journal of The Chemical Society Perkin Transactions I, pp. 2933–2936 (1980).

Hylands et al., "New Cucurbitacin Derivatives from Bryonia dioica Jacq.", J. Chem. Soc. Perkin Trans. I, pp. 2821–2825 (1983).

Kirschmann et al., "Letter to the Editor: Recent Food Poisoning from Cucurbitacin in Traditionally Bred Squash", Fd Chem. Toxic, vol. 27, No. 8, pp. 555–556 (1989).

Lance et al., "Field–Cage Tests of Semiochemical–Based Toxic Baits for Diabrotica Beetles: Effects of Particle Distribution an Attractant Content", Abstract fro ESA–NCB Meeting, Grand Rapidds, MI (Mar. 1990).

Lance et al., "Semiochemical–Based Toxic Baits for *Diabrotica vigifera virgifera* (Coleoptera: Chrysomelidae): Some Effects of Particle Distribution and Attractant Content", J. Econ. Entomol. Forage and Row Crops.

Lance et al., "Field–Cage and Laboratory Evaluations of Semiochemical–Based Baits for Managing Western Corn Rootworm (Coleoptera: Chrysomelidae)", Journal of Economic Entomology, vol. 83, No. 3, pp. 1085–1090 (Jun. 1990).

Lance et al., "Field Tests of Semiochemical–based Toxic Baits for Suppression of Corn Rootworm Beetles (Coleoptera: Chrysomeliadae)", Manuscript for J. Econ. Entomol. Forage and Row Crops (Mar. 1991).

Lance et al., "Semichemical–Based Toxic Baits for *Diabrotica vigifera virgifera* (Coleoptera: Chrysomelidae): Effects of particle Size, Location and Attractant Content", Journal of Economic Entomology, vol. 84, No. 6, pp. 1861–1868 (Dec. 1991).

Levine et al., "Control of Western Corn Rootworms with Semiochemical Baits in Illinois", Abstract Presented at Entomological Society of American North Central Branch Meeting, Mar. 1990.

Mason et al., "Cucurbitacin–Adulterated Diet is Avoided by Captive European Starlings", Cucurbitacins: J. Wildl. Manage 54:(4), pp. 672–676 (1990).

Mata et al., "Chemical Studies on Mexican Plants Used in Traditional Medicine v. Cucurbitacin Glucosides From Cigarrilla, Mexicana", Journal of Natural Products, vol. 51, No. 5, pp. 836–839 (Sep.–Oct. 1988).

Mata et al., "Secondary Metabolites From Hintonia Latiflora", Phytochemistry, vol. 29, No. 6, pp. 2037–2040 (1990).

Meinke, "1985 Adult Western Corn Rootworm Suppression Study, Large Scale Griffin Formulation Evaluation", paper for Department of Entomolgy, University of Nebraska, Lincoln, NE, pp. 1–4 (1985).

Meinke et al., "Pheromone Delivery System: Western Corn Rootworm (Coleoptera: Chrysomelidae) Pheromone Encapsulations in a Starch Borate Matrix", Journal of Economic Entomology, vol. 82, No. 6, (Dec. 1989).

Metcalf et al., "Cucurbitacins as kairomones for diabroticite beetles", Proc. Natl. Acad, Sci. USA, vol. 77, No. 7, pp. 3769–3772 (Jul. 1980).

Metcalf et al., "Cucurbitacin Contents and Diabroticite (Coleoptera: Chrysomelidae) Feeding upon *Cucurbita spp.*", Environ. Entomol., vol. 11, No. 4, pp. 931–937 (Aug. 1982).

Metcalf et al., "Controlling Cucumber Beetles and Corn Rootworm Beetles with Baits of Bitter Cucurbit Fruits and Root", CGC 6:79–81 (1983).

Metcalf, "Coevolutionary Adaptions of Rootworm Beetles (Coleoptera: Chrysomelidae) to Cucurbitacins", Journal of Chemical Ecology, vol. 12, No. 5 (1986).

Metcalf et al., "Dry Cucurbitacin–containing Baits for Controlling Diabroticite Beetles (Coleoptera: Chrysomelidae)", Journal of Economic Entomology, vol. 80, No. 4, pp. 870–874 (Aug. 1987).

Metcalf et al., "The Chemical Ecology of Diabroticites and Cucurbitaceae", Experimentia 45, pp. 240–247 (1989).

Moerman, "Medicinal Plants of Native America", University of Michigan Museum of Anthropology, Technical Reports, vol. 1, No. 19 (1986).

Mullin et al., "Feeding and toxic Effects of Floral Sequiterpene Lactones, Diterpenes, and Phenolics from Sunflower (*Helianthus annuus I.*) and Western Corn Rootworm", Journal of Agricultural and Food Chemistry, vol. 39, No. 12, pp. 2293–2299 (1991).

Nabhan et al., "Wild Cucurbita in Arid America: Ethnic Uses, Chemistry and Geography", An Annotated Bibliography, (1985).

Nelson et al., "Effect of Plant Population and Planting Date on Root and Starch Production of Buffalo Gourd Grown as an Annual", Reprint from J. Amer. Soc. Hort. Sci. 108(2):198–201 (Mar. 1983).

Nelson et al., "Irrigation and Plant Spacing Effects on Seed Production of Buffalo and Coyote Gourds", Reprint from Agronomy Journal, vol. 80, No. 1, pp. 60–65 (1988).

Nelson et al., "Irrigation Effects on Water Use, and Production of Tap Roots and Starch of Buffalo Gourd", Reprint from Agronomy Journal, vol. 81, No. 3, pp. 439–442 (1989).

Nelson, "The Buffalo Gourd–Information on its Culture for Root and seed Production", paper for University of Arizona, Maricopa Agricultural Center, pp. 1–6 (1990).

Nishida et al., "Sequestration of Distasteful Compounds By Some Pharmacophagous Insects", Journal of Chemical Ecology, vol. 15, No. 1, pp. 151–164 (1990).

Paul, "Getting Tricky with Rootworms: Here's a twist on the old bait–and–switch game", Agrichemical Age, pp. 6, 25E, and 30 (Mar. 1989).

Perring et al., "Research Reveals Pattern of Cucurbit Virus Spread", California Agriculture, vol. 46, No. 2, pp. 25–40 (Apr.–Mar. 1992).

Pitrat, "Linkage Groups in *Cucumis melo L.*", Journal of Heredity, 82:406–411 (1991).

Raemisch et al., "Field Tests for an Adult Western Corn Rootworm Aggregation Pheromone Associated with the Phagostimulatory Characteristic of Bitter *Cucurbita spp.*" J. Agric. Entomol. 1(4):339–344 (Oct. 1984).

Rehm et al., "Bitter Principles of the Cucurbitaceae. VII–The Distribution of Bitter Principles in this Plant Family", J. Sci. Food Agric., vol. 8, pp. 379–688 (Dec. 1957).

Rhodes et al., "Diabroticite Beetle Responses to Cucurbitacin Kairomones in Cucurbita Hybrids", J. Amer. Soc. Hort. Sci. 105(6):838–842 (1980).

Rice et al., "Chromatographic and Mass Spectral Analysis of Cucurbitacins of Three *Cucumis sativus* Cultivars", J. Agric. Food Chem., vol. 29, pp. 194–196 (1981).

Rymal et al., "Squash Containing Toxic Cucurbitacin Compounds Occurring in California and Alabama", Journal of Food Protection, vol. 47, pp. 270–271 (Apr. 1984).

Sakr et al., "Viability of Seeds Harvested from Fruits at Different Stages of Maturity", American Society for Horticultural Science, vol. 60, pp. 327–329 (1952).

Scheerens et al., "Buffalo Gourd: Composition and Functionality of Potential Food Ingredients", Cereal Foods World, vol. 31, No. 2, pp. 183–192 (Feb. 1986).

Sharma et al., "Influence of Cucurbitacins, Sugar and Fatty Acids on Cucurbit Susceptibility to Spotted Cucumber Beetle", J. Amer. Soc. Hort. Sci. 96(5):675–680 (1971).

Stoewsand et al., "Toxicologic Response in Mice Fed Cucurbita Fruit", Journal of Food Protection, vol. 48, No. 1, pp. 50–51 (Jan. 1985).

Stuppner et al., "New Cucurbitacin Glycosides from *Picrorhiza kurrooz*", Planta Medica 55, pp. 559–563 (1989).

Sutter et al., "New Strategies for Reducing Insecticide Use in the Corn Belt", Sustainable Agriculture Field Research and Education, pp. 231–249 (1991).

Tallamy, "Squash Beetle Feeding Behavior: An Adaptation Against Induced Cucurbit Defenses", Ecology, 66(5) pp. 1574–1579 (Oct. 1985).

Tallamy et al., "Variation and Function of Cucurbitacins in Cucurbita: An Examination of Current Hypotheses", The American Naturalist, vol. 133, No. 6, pp. 766–768 (Jun. 1989).

Tallamy et al., "Squash Beetles, Cucumber Beetles, and Inducible Cucurbit Responses", Phytochemical Induction By Herbiores, pp. 155–181 (1991).

Tollefson, "Treatment of Adult Corn Rootworms with a Semiochemical and Insecticide Mixture to Disrupt Oviposition and Subsequent Larval Damage" (1984).

Tollefson, "Control of Western Corn Rootworm Larvae Through Adult Supervision" (1985).

Trimnell et al., "Pesticide Encapsulation Using a Starch–Borate Complex as Wall Material", J. Appl. Poly. Sci., vol. 27, pp. 3919–3928 (1982).

Trimnell, "Starch Granules Strengthen Insect Attractants", Agrichemical Age, p. 20D (Feb. 1990).

Weissling et al., "Behavioral Responses of Diabrotica Adults to Plant–Derived Semichemicals Encapsulated in a Starch Borate Matrix", Weissling Dissertation, Chapter 1, [In Entomol. Exper. Appl., vol. 1, 53:219–228 (Aug. 1990)].

Weissling et al., "'Potential of Starch Encapsulated Semiochemical–Insecticide Formulations for Adult Corn Rootworm (Coleoptera: Chrysomelidae) Control ", J. Econ. Entomol. vol. 84, No. 2, pp. 601–609 (1991).

Weissling et al., "Potential of Starch Encapsulated Semiochemical/Insecticide formulations for Adult Dorn Rootworm (Coleoptera: Chrysomelidae) Control", Manuscript for J. Econ. Entomol., Forage and Row Crops (1987–1989).

Weissling, "Potential of Starch Encapsulated Semiochemical/Insecticide Formulations for Adult Corn Rootworm (Coleoptera: Chrysomelidae) Control", Weissling Dissertation, Chapter 2, [In J. Econ. Entomol.].

Weissling et al., "Effect of Starch–Based Corn Rootworm (coleoptera: Chrysomelidae) Baits on Selected Nontarget Insect Species: Influence of Semiochemical Composition", J. Econ. Entomol. vol. 84, No. 4, pp. 1235–1241 91991).

Weissling et al., "Effect of Starch–Based Corn Rootworm Baits on Selected Nontarget Insect Species: Influence of Semiochemical Composition", Abstract presented at the Entomological Society of America North Central Branch Meeting, Mar. 1990.

Weissling et al., "Semiochemical–Insecticide Bait Placement and Vertical Distribution of Corn Rootworm (Coleoptera: Chrysomelidae) Adults: Implications for Management", Entomological Society of America, vol. 20, No. 3, pp. 945–952 (Jun. 1991).

Young, "The Effect of Maturity and Storage on Germination of Butternut Squash Seed", American Society for Horticultural Science, vol. 53, pp. 345–347 (1949).

Yang et al., "Cucurbitacin Contents in *Hemsleya dolichocarpa*", American Journal of Chinese Medicine, vol. XIX, No. 1, pp. 51–56 (1991).

"Agronomic Potential of Buffalo Gourd as a Specialty Crop in New Mexico", Agricultural Experiment Station, Bulletin 740, New Mexico State University, College of Agriculture and Home Economics (Oct. 1988).

5,607,684

MANUFACTURE OF BAIT WITH HOT MELT BINDER

This application is a continuation in part of application Ser. Nos. 07/784,506 filed on Oct. 31, 1991 now U.S. Pat No. 5,484,587; 08/189,355 filed on Jan. 31, 1994 now U.S. Pat. No. 5,571,522; and 08/194,358 filed on Feb. 8, 1994 the disclosures of which are herein incorporated by reference.

FIELD OF THE INVENTION

The invention relates to a bait having a particularly effective form and structure for control of various insects and particularly for immature and adult diabroticine beetles.

BACKGROUND OF THE TECHNOLOGY

Diabroticine beetles are a significant problem during the growth of, inter alia, corn (field, pop, seed, and sweet), beans, Cucurbitaceae (including cucumbers, melons, squash, and pumpkins), peanuts, peas, potatoes, and sweet potatoes. Corn is conveniently used to describe the effects of diabroticine beetles. These pests are the direct or indirect (i.e., as a vector for bacteria and inoculation of melons and squash) cause of millions of dollars of crop and garden damage annually. Damage by these beetles has continued despite over 30 years of attempts at control.

Diabroticine beetles encompass multivoltine and univoltine species. Multivoltine species (e.g., the southern corn rootworm) can produce up to 3 generations a year. Univoltine species (e.g., northern and western corn rootworm) have a life cycle that starts with eggs laid 4–24 inches below the soil surface in the Fall. In early Spring and over the course of several weeks, the larvae (a form of immature beetle) hatch and begin to feed on nearby roots thereby destroying the root's anchoring abilities and the microhairs responsible for mineral, nutrients, and water assimilation. If the plant roots have not been so damaged that the plants falls over, the yield from the affected plants is reduced due to impaired nutrition.

After feeding, the diabroticine larvae pupate and emerge from the ground as adult beetles. Univoltinc beetles emerge at some time during mid July through August (depending on local climate). Male diabroticine beetles emerge about 1 week before the females (week 1) which, in turn, emerge at about the same time as corn silks emerge. Because the fresh silks emit a number of volatile agents which are attractive to both the male and female beetles, the 7–10 days of silking represents a period of high feeding activity for the beetles. The beetles immediately begin to migrate up the stalk toward the leaves, ears, and silks. This compulsion is quite strong since there is evidence that the beetles will not move down the corn stalk in response to attractants. Throughout this period, the beetles feed and mate.

The key to control of the diabroticine beetles is to disrupt the life cycle by affecting the immature and/or adult beetles. One method known in the art as "banding" refers to the practice of trying to control the larvae by applying a contact insecticide in or along a furrow containing planted seeds. The theory behind banding is that larvae will enter the treated area when searching for roots and die due to contact with the insecticide.

Unfortunately, microbial attack impairs the efficacy of insecticides in the soil well before all the larvae have had time to hatch and enter the treated band. Concerns for groundwater contamination, the impact on nontarget organisms (e.g., bird kill), and the hazards of human exposure to the toxic insecticides all restrict the use of soil insecticides that might be capable of surviving in the soil through the larval feeding stage.

The effectiveness of banding is also limited by the plants themselves. Plant roots often extend well beyond the treated band leaving the roots vulnerable to attack.

It has been proposed to use the tissue of dried gourds from the Cucurbitale order in combination with 0.01–10% by weight (wt %) of an insecticide to make a lethal bait for the control of diabroticine beetles. Due to genetic evolution, corn rootworm larvae have evolved to compulsively feed on cucurbitacins.

From Canadian Patent No. 1,195,922, the bitter tasting cucurbitacins in the gourd tissue acts as a compulsive feeding stimulant for diabroticine beetles but is a feeding deterrent to beneficial insects. By coating the gourd tissues with an insecticide according to the teachings of the disclosure, it was asserted that the beetles would compulsively consume a lethal quantity of insecticide.

It would be desirable to have a bait formulation that would provide a high level of efficacy against immature and mature diabroticine beetles when applied through conventional application equipment as a sprayable aqueous solution, as well as when applied as a dry granular bait.

Many baits are made by spray drying a mixture of materials to form a particulate solid. Spray drying is performed typically by passing an aqueous slurry of ground AI and a binder material (usually a number of materials based on alkylnaphthylene or alkylformaldehyde condensate, calcium silicate, kaolinite, diatomaceous clays) through a nozzle into a tower. The droplets are dried at a temperature of about 150° C. As the water is vaporized, the slurry droplets form the particulate product and are collected. Despite the high temperature drying, contact between the slurry water and the amount of residual adsorbed water in the binder can degrade many useful insecticides during storage.

It would be useful to have a manufacturing process that eliminated the need for contact with water to produce a bait that did not exhibit insecticide degradation due to hydrolysis.

SUMMARY OF THE INVENTION

It is an objective of the invention to provide a bait and method of use thereof having high levels of pest control and which is particularly effective against diabroticine populations.

It is another objective of the invention to provide a composition containing an intimate admixture of a feeding stimulant and insecticide in a form useful for application as a dry granular solid or as a solid suspended in aqueous solution using conventional application equipment.

In accordance with these and other objectives that will become apparent from the description herein, baits according to the invention are particulate composite baits comprising a homogeneous mixture of: (a) a binding agent comprising a polymer that is solid at 25° C. and exhibits a melting point within the range from about 35° C. to about 65° C.; (b) an erosion rate modifier for said binder; (c) 0.01–99 wt % of an insecticide; and (d) 0.01–99 wt % of a feeding stimulant for the target insect population.

The present bait provides bait in a physical form exhibiting high efficacy made by a water-free, continuous process. The homogeneous distribution of feeding stimulant assures that consumption of feeding stimulant will also include consumption of insecticide by target insects until a lethal dose is achieved. The use of a molten polymeric binder avoids the need for elevated temperatures to remove water from prior binder formulations that can adversely affect the storage stability of many insecticides.

DETAILED DESCRIPTION

The present invention provides a particulate bait containing a binder matrix of a meltable polymer having homogeneously dispersed therein a diabroticine feeding stimulant and an insecticide. The use of a meltable polymer permits the baits to be formed into solids by spraying the molten mixture into the top of a cooled congealing tower in a continuous, water-free process. (As used herein, the term "substantially water-free" denotes a process free of purposefully added water: any water found in the process is de minimis such as from environmental sources.) As the binder cools, the bait components form a particulate bait exhibiting a controlled particle size distribution. Bait is then collected, screened for optimum size, and packaged without significant further handling.

Depending on the diameter of the bait, the bait can be applied in the form of a dry granular solid or as an aqueous bait suspension applied through conventional spraying equipment.

1. Binder Component

Binders for the present bait include materials that are solid at 25° C. and exhibit a melting point within the range from about 35° C. to about 65° C. and that are: (a) palatable to target insects; and (b) able to bind together the insecticide and cucurbitacin components at field temperatures yet (c) pass through extruders, sprayers, and agglomeraters conventionally used to form particles. Materials that can be used as binders according to the invention include polyethylene glycols with a molecular weight within the range of about 1,000 to about 20,000; block copolymers of ethylene oxide and propylene oxide (EO/PO); solid fats (e.g., partially hydrogenated oils like soybean or cottonseed); and various mono-, di- or triglycerides.

Polyethylene glycol (PEG) useful in the present invention is commercially available in molecular weights ranging from 1,000 to 20,000 with melting points within the range of about −15° C. to 70° C. The PEG with a melting point within the range from about 37° C. to about 64° C. forms a nontacky, dry solid at room temperature that is particularly well suited as a binder for the present invention.

The EO/PO polymers are commercially available in a wide variety of physical and chemical characteristics from BASF Wyandotte Corporation, Performance Chemicals Division, Parsippany, N.J. U.S.A. under the PLURONIC™ name. These materials are sold as surfactants for emulsions, suspension stabilizers, and associative thickeners.

The binder of the bait is used in an amount within the range from about 1 wt % to about 95 wt % in a quantity sufficient to provide a structurally sound bait having insecticide and feeding stimulant components homogeneously dispersed therethrough. Preferably, the binder is used in an amount of about 1 wt % to about 50 wt % and more preferably within the range from about 1–35 wt % based on the total weight of the bait. A particularly preferred amount of gelatin as the binder is within the range from about 5–30 wt % based on the total bait weight.

Generally, the bait should be made to be able to withstand some exposure to water for spray application or to maintain a particulate structure in the treated area. The amount of water resistance will, however, depend on the application method, climate, field irrigation needs and cycle, etc.

The water solubility of the binder for the present invention is adjusted by adding thereto an erosion rate modifier. When added in a suitable quantity for the specific component, the water solubility of the binder is reduced to a level sufficient to provide a matrix system that is poorly or insoluble in water at 25° C. Particulate baits preferably exhibit a solubility in such cold water of less than about 5% by weight, preferably less than about 2 wt %, and most preferably less than about 1 wt % to be sprayed from conventional tank spraying equipment. Suitable erosion rate modifiers include zein, fatty acid-alkanolamides such as Monamid™ Grade S, ethylcellulose, shellac, and any other alcohol soluble/water insoluble materials.

Other modifiers can be used when PEG is the binder. See, Snipes U.S. Pat. No. 4,629,621 particularly in column 4, lines 1–10 the disclosure of which is herein incorporated by reference. Suitable erosion rate modifiers include $C_{12}$–$C_{20}$ fatty acids (e.g., lauric acid, myristic acid, palmitic acid, stearic acid, and arachidic acid); $C_{12}$–$C_{20}$ alcohols (e.g., lauryl alcohol, myristyl alcohol, palmityl alcohol, stearyl alcohol, and arachidyl alcohol); amphophilic esters of fatty acids with glycerol (e.g., monoesters of $C_{12}$–$C_{20}$ fatty acids with glyceryl monopalmitate); $C_{12}$–$C_{20}$ amines (e.g., lauryl amine, myristyl amine, palmityl amine, stearyl amine, and arachidiyl amine); and amides of $C_{12}$–$C_{20}$ fatty acids.

The erosion rate modifier is added in an amount sufficient to reduce the water solubility of the matrix system in 25° C. water. Such amounts are usually within the range of 0.1 wt % to about 10 wt %, generally within the range of about 2–8 wt %.

2. The Feeding Stimulant Component

Feeding stimulants useful in the present invention include materials that will act as gustatory stimulants, compulsory or otherwise, for the target population. Gustatory stimulants can be insect diet that provides nutrition upon consumption. Feeding stimulants useful for controlling diabroticine populations according to the present invention include any of the cucurbitacins (in solid or liquid form) or milled corn germ associated with less than about 25%, preferably less than about 10%, endosperm.

The cucurbitacin feeding stimulants are described in Canadian Patent No. 1,195,922; U.S. Pat. No. 4,880,624; and *The Merck Index,* 10th ed., p. 2609 (1983). Briefly summarized, plants in the cucurbitacae order contain small quantities of oxygenated tetracyclic triterpenoid compounds (usually referred to as the cucurbitacins) that are responsible for the bitter taste of the plant tissue. Although compulsively consumed by diabroticine populations, the cucurbitacins provide no known nutritional value to the insect. Seventeen of the cucurbitacins have been isolated and identified by letters, namely cucurbitacins A, B, C, D, E, F, G, H, I, J, K, L, O, P, Q, R, in aglycone (somewhat water soluble) or glycoside (very water soluble) forms. The cucurbitacins B, D, E, I aglycone or glycoside forms thereof are preferred feeding stimulants for baits of the present invention.

The cucurbitacin can be added to the bait as a dilute cucurbitacin-containing solid or liquid with a concentration of less than about 0.01 wt % cucurbitacin, as a purified compound, or as a concentrated liquid containing more than about 0.01 wt %, preferably more than about 0.05 wt %, and even more preferably within the range of 0.05–0.5 wt % cucurbitacins. The cucurbitacins can be added as discrete particles homogeneously distributed throughout the bait or as a liquid stream that is homogeneously distributed throughout the bait. The cucurbitacin-containing material are preferably added as a discrete plant tissue particles which contain cucurbitacins, cucurbitacin-containing liquids applied to solid carriers such as a corn cob grit, or introduced as a concentrated liquid that is mixed homogeneously into the matrix with the process liquid used to spray dry the baits. Particularly preferred forms for introducing a cucurbitacin feeding stimulant component are dried powders of dried plant tissues or as a concentrated cucurbitacin solution containing 20–50 wt % solids and about 0.1–0.5 wt % cucurbitacins.

Plant tissues containing the highest levels of cucurbitacins include the roots of the buffalo gourd (*Cucurbita foetidissima*) which, when dried, contain about 0.3% by weight cucurbitacins and fruits of cucurbitacin containing fruits. See, Metcalf Canadian Patent No. 1,195,922 for a list of cucurbitacin-rich plant species useful as cucurbitacin sources for the present invention. Other cucurbitacin-containing materials useful for the invention may come from, inter alia, *C. andreana* NAUD, *C. cylindrata* Wats, *C. ecuadorensis* Cutl. and Whir., *C. foetidissima* HBK, *C. gracilior* Bailey, *C. lundelliana* Bailey, *C. martinezii* Bailey, *C. okeechobensis* Bailey, *C. palmata* Wats., *C. palmeri* Bailey, *C. pedatifolia* Bailey, *C. sororia* Bailey, and *C. texana* Gray.

Buffalo gourd root powder is a preferred source of solid cucurbitacin-containing material for use as the feeding stimulant component in baits of the invention because the root powder contains a significant quantity of starch. This starch acts as a sticking agent when wetted to assist the applied bait particles in adhering to the plant surface. Such adhesion properties are advantageous when bait particles are aerially applied. If desired, however, starch (e.g., food starch) may be added to enhance the sticking effects whether cucurbitacin-containing plant tissues are used or some other form of cucurbitacin.

The use of cucurbitacin-containing plant tissues has a number of practical benefits. First, the inherent chemical composition of cucurbitacin-containing plant tissue is responsible for the compulsive feeding effects. Cucurbitacin-containing plant tissues can, therefore, be used in a dry form which reduces the special handling and storage concerns with grinding, formulating, and storing moist plant tissues. Moreover, the stimulation effects are found at such extremely low levels that there are no special handling procedures for handling the cucurbitacin which is quite toxic in its pure form. Only the insecticides might require special handling.

References herein the "cucurbitacin-containing" shall mean plant tissue solids and either solid or liquid carriers containing at least one of the cucurbitacins A, B, C, D, E, F, G, H, I, J, K, L, O, P, Q, R aglycone or glycoside forms of any of these.

3. Insecticide Component

Insecticides useful for the invention are those effective to control the insect populations by killing or sterilizing the immature or adult beetles. Generally, an amount within the range of 0.01–99 wt %, preferably 0.1–50 wt %, even more preferably an amount within the range of 0.01–25 wt %. A particularly preferred amount of insecticide is within the range from about 5–25 wt % based on the total weight of the bait.

Insecticides useful in the invention are materials and biological agents that control diabroticine populations through lethal ingestion, sterilization, or other interference with the diabroticine life cycle. Exemplary insecticides include solid and liquid forms of the carbamates (e.g., carbaryl, aldicarb, methomyl, carbofuran, bendiocarb, oxamyl, thiodicarb, trimethylcarb); organophosphates (e.g., phorate, terbufos, fonophos, isofenphos, ethoprop, fenamiphos, disulfoton, malathion, parathion, demeton, dimethoate, chlorpyrifos, diazinon, and phosmet); compounds which break down the beetle's digestive tract tissue including fluorine compounds (cryolite), zinc, and mercury; nicotine; rotenone; neem oil or azadiractin; natural or synthetic pyrethrins; petroleum oils; the halogenated hydrocarbons (e.g., endfin, aldrin and its epoxide, dieldrin, heptachlor, DDT, BHC, lindane, chlordane, methoxychlor, DDD, TDE, and the polychlorinated biphenyls); and microbials (e.g., *Bacillus thuringiensis* and entomopathic viruses such as diabroticidal viruses such as the bacculo viruses).

Most insecticides are commercially available in the form of a solid particle. Liquids may be used in the baits homogeneously mixed with the binder. The use of microencapsulated liquids or fine solids that become intimately bound are preferred for handling and control. In general, organophosphates and the carbamates are preferred with phorate, carbaryl and methomyl being most preferred.

Baits of the invention exhibit a surprisingly high level of diabroticine control while enabling the application of overall lower levels of insecticide relative to conventional practice. For example, the current EPA label application rate for control of diabroticine beetles by carbaryl is 454–908 grams active ingredient (AI) carbaryl per acre of treated area. With the present invention, however, the higher levels of control are realized by a significantly lower application rate. For carbaryl, this rate is within the range from about 2 to about 200 g AI/acre, preferably about 5–100 g AI/acre, and most preferably about 20–50 g AI/acre. Practical carbaryl formulations will translate into an application rate of 2–20 lbs. of bait per acre when formed as a dry granule using an inert carrier (such as corn cob grit or clay) or 5–50 ounces of bait applied from aqueous solution per acre.

The quantities of diabroticidal insecticides other than carbaryl are used in quantities proportional to their diabroticidal efficacy relative to the levels of carbaryl used herein. As an example, diabroticidal insecticides that are 50% as effective as carbaryl are used in quantities of 5–400 g AI/acre, but insecticides that are twice as effective are used in quantities within the range from about 1–100 g AI/acre. The precise application rate of any particular insecticide when supplied in baits of the present invention is readily determinable by one in this art with the exercise of no more than the existing skill level after consideration of the present disclosure.

Feeding stimulant and insecticide solids exhibiting a size of less than about 100 μm in diameter are well suited for the present invention. The invention is particularly useful for solids having a size within the range from about 0.1 μm to about 50 μm and even more useful for solids within the range of 2 μm to about 30 μm.

4. The Encapsulation Process

In the encapsulation process, finely divided or liquid feeding stimulant and insecticide are mixed into molten binder and formed into droplets. In general, finely divided solids must be first ground to size with conventional techniques if the solid is not commercially available in a pre-ground form.

The bait components are added to a molten binder containing any additives and mixed. Molten binder is preferably melted in a stirred, jacketed vessel to control the melting temperature. The molten binder preferably exhibits a viscosity of less than about 1000 cp, more preferably less than about 500 cp, and most preferably less than about 100 cp to allow particle formation through conventional nozzles and extrusion equipment.

If, after a solid component is added, the viscosity of the molten binder/solids mixture is found to be greater than about 500 cp, a solvent for the binder should be used to reduce viscosity. Any solvent is, however, preferably added to the molten binder before adding the solids. Such a solvent will depress the solidification point of the binder in proportion to the amount of solvent used, so some process adjustment may have to be made as noted below to solidify the solids. Solvents that can be used for reducing the viscosity of PEG include: alcohols (e.g., isopropyl alcohol, and methyl alcohol) acetone, CELLOSOLVE™ (made from butylcellulose); ethyl acetate, and toluene.

The encapsulation of liquid feeding stimulant and/or insecticide does not generally need a solvent. The added liquid will act as a solvent for the binder and reduce the viscosity accordingly. At some concentration level that is unique to each active ingredient, however, no additional liquids can be carried by the binder. Attempting to add more liquid component adversely affects the structural integrity of the resulting particle. At very high concentrations, e.g., greater than about 70 wt % for some materials, the amount of binder is insufficient to impart integrity to the microcapsule. An overloaded particle is friable and cannot maintain a structurally intact particle form with even moderate pressure thereby breaking apart and forming undesired fines. Rolling the formed particles between the thumb and forefinger with a moderate crushing pressure will readily reveal whether the loading limit of the binder has been exceeded.

The structural integrity of the particle can be enhanced by adding to the molten binder a second film-forming polymer to enhance strength. Preferred second polymers are alcohol and water soluble with a tensile strength of greater than about 2000 psi and an elongation of greater than about 10%. Solubility of the added film-forming polymer in alcohol will ensure chemical compatibility with the binder, and water solubility will assure that the dispersability and dissolution characteristics of the particle are not significantly affected.

Generally, no more than about 0.001–10 wt % of the strength enhancing second film-forming polymer is sufficient to enhance the structural integrity of a particle formed therefrom. Preferably, the second film-forming polymer is used in an amount within the range from about 0.001 wt % to about 5 wt %, even more preferably within the range of 0.1–1 wt %, based on the amount of the binder.

Preferred second film-forming polymers for enhancing the strength of the resulting particle include cellulose derivatives (i.e., hydroxypropyl cellulose, hydroxyethyl cellulose); polyethylene oxide; polyvinylpyrrolidone, and hydroxypropyl guar.

Solid or encapsulated forms of one or more spray adjuvants can be carried in the binder. Suitable adjuvants include spreader-stickers, nonionic surfactants (e.g., calcium dodecylbenzenesulfonate salts, nonyl and octyl phenolethoxylates, and alkyl naphthylene sulfonates), liquid emulsifiers (e.g., sorbitol esters), dispersing agents (lignin sulfonates and salts thereof), and ultraviolet screening agents (e.g., titanium dioxide, zinc oxide, carbon black, congo red, para-aminobenzoic acid, and the benzophenones).

Once thoroughly mixed into a homogeneous material, the temperature of the mixed, molten material is lowered in the stirred vessel to a temperature above the solidification temperature of the molten, homogeneously mixed material. Preferably, the temperature is lowered to a temperature of no more than about 5°–15° C. above the solidification temperature. The specific temperature will depend on the particular binder material used as well as any solvents that have been added. Preferably, the mixture will exhibit a melting point within the range from about 40° C. to about 70° C.

In general, cooling the molten material inside the stirred, jacketed vessel is less expensive and more flexible than constructing a congealing tower or zone that is tall enough to accommodate the required degree of cooling for all possible formulations made by the present invention.

Once cooled to the desired temperature, the molten binder/bait component mixture is sprayed downwardly through any droplet forming device (e.g., nozzles or circular disks exhibiting holes sized to the particle size desired) into the top of a congealing tower or zone. As the droplets fall through the cooling area, they solidify as they cool to a temperature (e.g., less than about 70° C., and more preferably less than about 40° C.) below the melting point of the mixture (i.e., the binder and any additives) and form particulate baits.

If a solvent has been used to increase loading, the temperature surrounding the device or heated device within the congealing tower should be maintained at a temperature above the flash point of the solvent but below the melting point of the binder. Solvent flashed from the particles can be recovered and reused with conventional vapor recovery systems.

To reduce the occurrences of plugging, the molten binder/bait component mixture can be sprayed into a congealing tower through heated nozzles or a heated rotating disk. Preferably, the nozzles or disk are heated to a temperature of at least about 10° C. above the solidification temperature of the binder/bait component mixture. In its most preferred form, a stainless steel disk atomizer is heated with a radiant heater located below the disk and directed upwardly against the bottom of the disk. Virtually any other form of heat can, however, be used. The nozzles or disk are preferably heated to a temperature within the range from about 30° C. to about 50° C. while the congealing tower is cooled by an upwardly flowing stream of air at a temperature within the range from about 5° C. to about 20° C. An air diverter is preferably used for shielding the heated nozzles from contact with the rising cool air. In effect, the diverter is used to divide the cooling tower into a heated zone immediately around the droplet forming orifices and a cooling zone around the periphery for cooling the droplets into solid particles.

The air flow rate is selected to produce a falling rate to allow sufficient time for the particle to solidify completely by the time the particle reaches the collection area at the bottom of the tower. For particles with a diameter of about 300–600 μm, a congealing tower height of about 1–2 m is generally sufficient.

Solid product particles can be collected easily because the solids are dry and non-tacky at the exit from the congealing zone. In the laboratory, solid product can be collected on a tarp or mat. Commercial processes may wish to use more efficient collection means with chutes, weighing sections, and automatic packaging devices.

If intended for application through conventional spraying equipment, the baits are desirably formed into a roughly spherical bait having a diameter of less than about 1000 μm. Preferably, 100% of the bait exhibits a particle size within the range from about 100 μm to about 600 μm. Particularly effective particle sizes are when 100% of the bait particles are within the range of about 150 μm to about 500 μm. For homogeneously formed particles within these ranges, consumption of the feeding stimulant will necessarily involve consumption of the insecticide.

Dry granular baits, on the other hand, will generally exhibit a larger corresponding size within the range from about 800 μm to about 2000 μm. Within the range of about 600–800 μm, the baits can be used as either a sprayable bait or a dry granular bait depending on the cold water solubility of the binder employed.

One method for applying dry bait particles that has proven to be acceptable is to form a dispensable solid made by loading dry corn cob grit having a size of 40–60 mesh (250–360 μm) with spray dried microsphere bait particles according to the invention. These corn cob particles have an open network of pores that will readily hold fine bait particles such as those of the invention yet present a sufficiently large particle size that the grit particles can be applied aerially without experiencing significant amounts of lost material due to bouncing off the plant surfaces upon landing. Preferably, porous carriers for the present bait particles have a bulk density of about that of corn cob grit.

In practice, it has been found that the diabroticine beetles will consume bait particles from within the openings of the grit or those that have fallen out as a result of landing on the plant surface. Either mode of consumption results in a high rate of kill.

Alternatively, a plurality of <600 μm preformed baits, such as those dispersed by spraying, can be deposited on a grit carrier and held thereon with the same binder as in the bait or a different binder.

5. Additional Additives.

A number of additional materials can be included in the baits of the present invention. For example, a preservative can be added in an amount sufficient to inhibit or prevent deterioration during storage and transport. Suitable preservatives include a material commercially available under the trademark Proxell™ and sodium benzoate. Suitable amounts of preservatives are within the range from about 0.05 wt % to about 1 wt %, preferably in an amount within the range of about 0.05–0.4 wt %.

Clays can be used to increase the density of the bait particle when bait according to the invention is formed as a dry granular bait that is distributed without spraying. Clay is added to form a bulk bait density within the range of about 25 to about 50 $lb/ft^3$ (400–800 $kg/m^3$), preferably within the range of about 30–40 $lb/ft^2$ (480–640 $kg/m^3$), and even more preferably about 35 $lb/ft^3$ (560 $kg/m^3$). Clays useful in the invention include kaolin, montmorrilonite, attapulgite, and bentonite. Generally, such clays are used as a bait component in an amount within the range from about 1 wt % to about 30 wt %, preferably, about 5 wt % to about 20 wt %.

Silica can be used in the bait as a binder component to modify extrusion flow characteristics, methods of bait formation, and to alter the density of the final bait. Many forms of silica can be used, but fumed silica having a particle size of less than about 5 microns is preferred. Silica can be used in an amount within the range from about 5–30 wt %, preferably within the range from about 20–30 wt %.

The baits may also contain one or more attractants for the target insect. Attractants such as those in U.S. Pat. No. 4,880,624 (incorporated herein by reference) are preferred for diabroticine insects.

Acceptance and palatability of the bait can be enhanced by adding plasticizers (e.g., sorbitol, maltodextrin), food starch, gums (e.g., sodium carboxymethylcellulose, carrageenan, and gellan), and protein sources such as pork gelatin.

6. Insects Controlled By the Present Baits

The present invention provides a method of using the baits to control insect infestations in a variety of plants. It should be noted that the term "insect" is used herein to denote the control of either immature or adult stages or both immature and adult stages so long as either form consumes solid food for sustenance and growth. In some multivoltine insect species exhibiting overlapping generations, application of the present baits can be used to control both adults and immature forms thereof simultaneously.

Insects that can be controlled with the present invention include insects of the diabroticine genus as well as cutworms, wireworms, billbugs, seed corn maggots, grubs, lesser corn stalk borer, seed corn beetle, flea beetles, European and Southwestern corn borer, fire ants and other ant species, onion maggots, sweet potato weevils, root maggots, and other types of chewing insects that feed on a variety of plants and whose feeding is stimulated by cucurbitacins.

Specific diabroticine insects that are advantageously controlled in accordance with the invention include the banded cucumber beetle (*Diabrotica balteata*), the green maize beetle (*Diabrotica decolor*), the twelve-spotted cucumber beetle (*Diabrotica duodecimpunctata*), the northern corn rootworm (*Diabrotica barberi*), the southern corn rootworm or spotted cucumber beetle (*Diabrotica undecimpunctata howardi*), the western spotted cucumber beetle (*Diabrotica undecimpunctata undecimpunctata*), the western corn rootworm (*Diabrotica virgifera virgifera*), the striped cucumber beetle (*Acalymma vittata*), Western striped cucumber beetle (*Acalymma trivittata*), the Mexican corn rootworm (*Diabrotica virgifera zeae*), *Diabrotica adelpha, D. speciosa speciosa, D. speciosa vigens, D. viridula, D. cristata, D. undecimpunctata sensulato, D. undecimpunctata tenella,* and *D. undecimpunctata duodecimnotata.*

7. Population Control with Baits

When used as adulticides on diabroticine insects, bait particles of the present invention are applied to the plant surfaces just before emergence of the adult diabroticine beetles or when monitoring counts indicate an economic level of infestation. For corn, an economic infestation level for treatment is about 0.5–1 beetles per plant at prevailing crop values and treatment costs. If an economic level of infestation is not seen, commercial fields are not considered to be economically justified for treatment because the losses sustained by beetle damage are worth less than the cost of an average treatment.

Plants that can be protected according to the present invention include virtually any plant affected by diabroticine beetles. Examples of such plants include, inter alia, corn (field, pop, seed, and sweet), beans, Cucurbitaceae (including cucumbers, melons, squash, and pumpkins), peanuts, peas, potatoes, and sweet potatoes.

An example of treating corn serves as a convenient tool for illustrating the invention. At 7–10 days after first emergence of the adult beetles in corn, the beetle population will be at its peak. Baits of the present invention should on the plants by this time and remain effective for 1–3 weeks to cover overlapping beetle emergence and migration periods. This timing and duration maximize the control over beetles that will produce the progeny causing the succeeding year's root damage.

Dry particles or a liquid suspension of the bait particles are distributed over the tops of the plants to be treated by conventional ground or aerial spraying and equivalent methods with or without herbicides and/or plant nutrients that do not adversely affect the activity of the bait. The objective of such application methods is to deposit bait particles on the upper surfaces of the plant where the diabroticine beetles will locate them while foraging for food.

When used as a larvacide for diabroticine insects at planting, baits are applied to the soil in a furrow containing plant seeds or along at least one of the sides of the seed-containing furrow. Similarly, the baits can be applied post-emergent to or along a furrow containing plants.

When applied to the soil, the bait is applied at a rate corresponding to about 400 grams of active insecticidal ingredient per acre or less. Preferably, the baits are applied in the same manner as the conventional practice of banding at a rate within the range from about 100 to about 200 grams of active diabroticidal insecticide per acre. Immature beetles will feed on the cucurbitacin and, due to the structure of the bait, consume or contact a lethal quantity of the associated insecticide.

EXAMPLES

Examples 1–6

Baits according to the present invention were made from the formulations in Table 1.

TABLE 1

| Example | Weight % | Component |
|---|---|---|
| 1 | 41.3 | Polyethylene Glycol (Carbowax ™ 4600) |
|   | 13.7 | Carbaryl (99% purity, <50 μm) |
|   | 40.0 | Buffalo Gourd Root powder |
|   | 5.0 | Monamid ™ S |
| 2 | 41.3 | Polyethylene Glycol (Carbowax ™ 4600) |
|   | 13.7 | Carbaryl (99% purity) |
|   | 40.0 | Buffalo Gourd Root powder |
|   | 5.0 | zein in a 90% alcohol/water solution |
| 3 | 76.0 | Polyethylene Glycol (Carbowax ™ 4600) |
|   | 13.7 | Carbaryl (99% purity) |
|   | 10.0 | Monamid ™ S |
|   | 0.3 | Cucurbitacin E glycoside solution |
| 4 | 81.0 | Polyethylene Glycol (Carbowax ™ 4600) |
|   | 13.7 | Carbaryl (99% purity) |
|   | 5.0 | zein in a 90% alcohol/water solution |
|   | 0.3 | Cucurbitacin E glycoside solution |
| 5 | 70.3 | Polyethylene Glycol (Carbowax ™ 3350) |
|   | 13.7 | Carbaryl (99% purity) |
|   | 6.0 | fatty acid amide (Monamid ™ S) |
|   | 10.0 | Cucurbitacin E glycoside solution |
| 6 | 55.3 | Polyethylene Glycol (Carbowax ™ 3350) |
|   | 13.7 | Carbaryl (99% purity) |
|   | 6.0 | fatty acid amide (Monamid ™ S) |
|   | 15.0 | Kaolin clay (WilKlay ™ FE) |
|   | 10.0 | Cucurbitacin E glycoside solution |

The baits of examples 5 and 6 were tested for acceptance and effectiveness in the control of adult diabroticine beetles. Each test was conducted with 15 beetles under the same conditions.

TABLE 2

| Bait | Mortality Rate After Exposure (%) | | | | | |
|---|---|---|---|---|---|---|
|  | 1 hr. | 2 hrs. | 3 hrs. | 4 hrs. | 5 hrs. | 24 hrs. |
| Ex. 5 | 38 | 73 | 73 | 73 | 73 | 89 |
| Ex. 6 | 40 | 75 | 89 | 89 | 89 | 91 |

The examples presented herein are intended to serve as an aid to understanding the present invention. Specific materials and particle sizes exemplified are not intended to serve as a limitation on the scope of the appended claims.

We claim:

1. A method for making baits useful for controlling insect populations, said method comprising the steps of:

forming droplets of a homogeneous, substantially water-free mixture comprising:
(a) 0.01–99 wt % of a feeding stimulant in the form of a finely divided particulate or liquid;
(b) 0.01–99 wt % of an insecticide; and (c) a molten, polymeric binder composition that is solid at 25° C. and exhibits a melting point within the range from about 35° C. to about 65° C. by passing said mixture through holes to form a desired particle size; and making solid bait particles from said droplets by cooling said droplets to a temperature below the melting point of said mixture.

2. The method of claim 1 wherein the forming step comprises:

forming said droplets by spraying said mixture through holes in a rotating nozzle or disk that has been heated to a temperature of at least about 10° C. higher than the melting point of said mixture.

3. The method of claim 1 wherein the forming step comprises:

forming said droplets into droplets with a size of less than 2000 μm.

4. The method of claim 1 wherein the forming step comprises:

forming said droplets into droplets with a size within the range of about 800 to about 2000 μm.

5. The method of claim 1 wherein the forming step comprises:

forming said droplets into droplets with a size of less than 1000 μm.

6. The method of claim 1 wherein the forming step comprises:

forming said droplets into droplets with a size within the range of about 150 μm to about 500 μm.

7. The method of claim 1 wherein particulate baits are made by forming said droplets and cooling said droplets to a temperature of less than about 40° C.

8. The method of claim 1 wherein droplets further comprise an erosion rate modifier.

9. The method of claim 1 further comprising:

making dispensable solids from said bait particles by loading corn cob grits with said bait particles.

10. A method for making baits useful for controlling insect populations, said method comprising the steps of:

forming droplets of a homogeneous, substantially water-free mixture comprising:
(a) 0.01–99 wt % of a feeding stimulant in the form of a finely divided particulate or liquid;
(b) 0.01–99 wt % of an insecticide; and (c) a molten, polymeric binder composition that is solid at 25° C. and exhibits a melting point within the range from about 35° C. to about 65° C. by passing said mixture through holes to form a desired particle size at the top of a congealing zone having a height sufficient to allow said droplets to cool and solidify into discrete, solid particles after passing through said congealing zone; and making particulate baits from said particles.

11. The method of claim 10 wherein the forming step comprises:

forming said droplets by spraying said mixture through holes in a rotating nozzle or disk that has been heated to a temperature of at least about 10° C. higher than the melting point of said mixture.

12. The method of claim 10 wherein the forming step comprises:

forming said droplets into particles with a size of less than 2000 μm.

13. The method of claim 10 wherein the forming step comprises:

forming said droplets into particles with a size within the range of about 800 μm to about 2000 μm.

14. The method of claim 10 wherein the forming step comprises:

forming said droplets into particles with a size of less than 1000 μm.

15. The method of claim 10 wherein the forming step comprises:

forming said droplets into particles with a size within the range of about 150 μm to about 500 μm.

16. The method of claim 10 wherein particulate baits are made by forming said droplets and cooling said droplets to a temperature of less than about 40° C.

17. The method of claim 10 wherein said mixture further comprises an erosion rate modifier.

18. The method of claim 10 further comprising:

making particulate baits by loading corn cob grits with said particles.

* * * * *